United States Patent [19]

Mori et al.

[11] Patent Number: 5,035,880
[45] Date of Patent: Jul. 30, 1991

[54] DENTIFRICE COMPOSITION

[75] Inventors: Shigeki Mori, Takatsuki; Naomi Yokosuka, Daito, both of Japan

[73] Assignee: Sunstar Kabushiki Kaisha, Osaka, Japan

[21] Appl. No.: 563,185

[22] Filed: Aug. 6, 1990

[30] Foreign Application Priority Data

Sep. 25, 1989 [JP] Japan ................................. 1-248664

[51] Int. Cl.$^5$ ................................................ A61K 7/22
[52] U.S. Cl. .......................................... 424/54; 424/49
[58] Field of Search .................................... 424/49, 54

[56] References Cited

U.S. PATENT DOCUMENTS

| | | | |
|---|---|---|---|
| 4,188,372 | 2/1980 | Gaffar | 424/54 |
| 4,224,309 | 9/1980 | Gaffar et al. | 424/54 |
| 4,370,314 | 1/1983 | Gaffar | 424/54 |
| 4,584,189 | 4/1986 | Leipold | 424/54 |

*Primary Examiner*—Shep K. Rose
*Attorney, Agent, or Firm*—Wegner, Cantor Mueller & Player

[57] ABSTRACT

A dentifrice composition stably containing cetylpyridinium chloride and having improved shape retention at a low temperature in the form of an aqueous gel is disclosed. The composition comprises 15 to 80% by weight of a polyoxyethylene-polyoxypropylene block copolymer surfactant based on the total weight of the composition, 0.001 to 5% by weight of cetylpyridinium chloride based on the total weight of the composition, and polyethylene glycol having an average molecular weight of 2,000 to 20,000 in a proportion of 1/200 to ¼ based on the weight of the polyoxyethylene-polyoxypropylene block copolymer.

4 Claims, No Drawings

DENTIFRICE COMPOSITION

FIELD OF INVENTION

The present invention relates to a dentifrice composition. More particularly, it relates to a dentifrice composition stably containing a cationic bactericide, cetylpyridinium chloride as an effective ingredient.

BACKGROUND OF THE INVENTION

Cetylpyridinium chloride is a cationic bactericide useful for inhibiting formation of dental plaque and it has hitherto been proposed to add it to dentifrices. However, since ingredients used in conventional dentifrices such as foaming agents and the like are normally anionic, cetylpyridinium chloride reacts with them, which results in a loss of its bactericidal activity. Accordingly, when it is used, measures for stabilizing cetylpyridinium chloride should be taken.

Under these circumstances, the present inventors have studied to stably formulate cetylpyridinium in a dentifrice. As a result, it has been found that an aqueous gel comprising a polyoxyethylene-polyoxypropylene block copolymer surfactant has desired properties as a dentifrice, and can specifically stabilize cetylpyridinium chloride.

An aqueous gel comprising a polyoxyethylene-polyoxypropylene block copolymer surfactant is disclosed in U.S. Pat. No. 3,740,421 for using in various fields such as cosmetics and drugs, and has been already known. However, such an aqueous gel has a problem that phase transition from gel to sol is caused at a low temperature, which results in a lowering of viscosity, as disclosed in International Journal of Pharmaceutics, 39 (1987), pages 121 to 127. Accordingly, when such an aqueous gel is used for the preparation of a dentifrice composition, there are problems such as deterioration of shape retention at a low temperature due to a lowering of viscosity, impairment of feeling of use, and solid-liquid separation due to sedimentation of a polishing agent, which makes the preparation of the dentifrice composition difficult.

OBJECTS OF THE INVENTION

In order to solve such problems and to obtain a dentifrice composition stably containing cetylpyridinium chloride which has improved stability at a low temperature, the present inventors have further studied intensively. As a result, it has been found that the desired objectives can be attained by using polyethylene glycol having a specific molecular weight.

The main object of the present invention is to provide a dentifrice composition stably containing cetylpyridinium chloride as an effective ingredient.

This object as well as other objects and advantages of the present invention will become apparent to a person skilled in the art from the following description.

SUMMARY OF THE INVENTION

According to the present invention, there is provided a dentifrice composition in the form of an aqueous gel comprising 15 to 80% by weight of a polyoxyethylene-polyoxypropylene block copolymer surfactant based on the total weight of the composition, 0.001 to 5% by weight of cetylpyridinium chloride based on the total weight of the composition, and polyethylene glycol having an average molecular weight of 2,000 to 20,000 in a proportion of 1/200 to ¼ based on the weight of the polyoxyethylene-polyoxypropylene block copolymer.

DETAILED DESCRIPTION OF THE INVENTION

The polyoxyethylene-polyoxypropylene block copolymer surfactant to be used in the present invention is a known surfactant composed of polyoxyethylene-polyoxypropylene glycol and is commercially available under the trade name of "PLURONIC" by BASF Corporation, U.S.A. In general, the surfactant is chemically defined by the molecular weight of a polyoxypropylene hydrophobic portion and the amount (% by weight) of a polyoxyethylene hydrophilic portion in the total molecular weight. A preferred surfactant is that wherein the molecular weight of the hydrophobic group (polyoxypropylene) is 1,400 to 4,000 and the amount of the hydrophilic group (polyoxyethylene) in the total molecular weight is in the range of 30 to 80% by weight.

The polyoxyethylene-polyoxypropylene block copolymer surfactant is added to the composition in an amount of 15 to 80% by weight, preferably, 20 to 50% by weight based on the total weight of the composition. When the amount of the surfactant added is less than 15% by weight, gelation is insufficient and, therefore, a problem of stability due to solid-liquid separation is caused. On the other hand, when the amount exceeds 80% by weight, gelation is too strong and a viscosity suitable for a dentifrice can hardly be obtained.

The polyethylene glycol used in the present invention is that having an average molecular weight of 2,000 to 20,000. Polyethylene glycol is used for improving stability at a low temperature of the polyoxyethylene-polyoxypropylene block copolymer surfactant and, when the average molecular weight thereof is less than 2,000, the effect on inhibition of a lowering of viscosity at a low temperature is insufficient. When the average molecular weight exceeds 20,000, problems such as low water solubility and the like are caused during the production steps. Polyethylene glycol is added in a weight ratio of 1/200 to ¼ based on the weight of polyoxyethylene-polyoxypropylene block copolymer surfactant. When the amount is less than 1/200, the effect on inhibition of a lowering of viscosity at low temperature is insufficient. When the amount is more than ¼, gelation by the polyoxyethylene-polyoxypropylene block copolymer surfactant is inhibited and, therefore, gelation is too weak and a viscosity suitable for a dentifrice composition can hardly be obtained.

Such a polyethylene glycol can also exist as a by-product formed during the production of the polyoxyethylene-polyoxypropylene glycol and, in the present invention, polyethylene glycol including such a by-product should be contained in the composition in the above proportion.

Cetylpyridinium chloride used as an effective ingredient in the present invention is normally formulated in an amount of 0.001 to 5% by weight, preferably about 0.01 to 0.5% by weight based on the total weight of the composition. When the amount is less than 0.001% by weight, sufficient bactericidal activity is not expected and, when the amount is more than 5% by weight, the resulting dentifrice has irritant properties to oral mucosa, and it causes a problem in practical use.

The dentifrice composition of the present invention can be prepared in the form of a toothpaste, a paste and the like by a known method and, if desired, polishing agents, humectants, flavors, sweeteners and the other effective ingredients can be suitably formulated in so far as they do not influence the effect of the present invention.

As described hereinabove, according to the present invention, a dentifrice composition stably containing cetylpyridinium chloride and having good shape retention at a low temperature can be obtained.

The following Examples and Comparative Examples further illustrate the present invention in detail. In Examples and Comparative Examples, all percents are by weight unless otherwise stated.

EXAMPLES 1 to 4 AND COMPARATIVE EXAMPLES 1 to 5

According to the formulations as shown in Table 1, toothpastes were prepared by a conventional method. All the amounts of ingredients in Table 1 are % by weight.

Bactericidal activity and stability at a low temperature of the resulting toothpastes were determined by the following method.

Bactericidal activity test

Each toothpaste (about 6.0 g) was weighed and suspended in distilled water to give a supernatant. The resulting supernatant was diluted with distilled water so that the concentration of cetylpyridinium chloride became 0.0001%, 0.0002% and 0.0004%.

On the other hand, cetylpyridinium chloride was dissolved in distilled water so that the concentration thereof became 0.0001%, 0.0002% and 0.0004%. These solutions were used as standard solutions for determining minimum bactericidal concentration (hereinafter abbreviated as MBC).

To each sample (10 ml) prepared was added $10^8$ to $10^9$ CFU/ml of a *Streptococcus mutans* cell suspension (0.1 ml) and a bactericidal reaction was carried out in a water bath at 37° C. for 15 minutes. After completion of the reaction, one loopful of each sample was spread on a trypticase soy agar (TSA) plate containing 0.5% of polyoxyethylene monooleate and 0.07% of lecithin.

Then, it was incubated at 37° C. for 2 days under anaerobic conditions ($N_2/H_2/CO_2 = 85/10/5$) and MBC was determined.

MBC of the standard solution was 0.0002%.

The samples were evaluated according to the following criteria:

A: MBC of the sample tested was the same as that of the standard solution.

B: MBC of the sample tested was greater than that of the standard solution.

Low temperature stability test

Measurement of viscosity

A toothpaste was charged in a glass bottle and allowed to stand at 25° C. and −5° C. for a week. Then, viscosity at each temperature was measured. Brookfield viscometer and Helipas spindle F were used and the measurement was carried out at 20 r.p.m. for one minute. The change of viscosity variation between both temperatures was defined as follows:

$$\text{Viscosity retention at low temperature (\%)} = \frac{\text{Viscosity at } -5° \text{ C.}}{\text{Viscosity at } 25° \text{ C.}} \times 100$$

Low temperature shape retention

The toothpaste is packed in a laminate tube and allowed to stand at −5° C. for a week. After that, the toothpaste was squeezed out from the tube. Solid-liquid separation was visually observed and evaluated according to the following criteria:

A: No solid-liquid separation was observed.

B: Solid-liquid separation was observed.

Finally, overall stability at a low temperature was evaluated according to the following criteria:

A: Viscosity retention was 80% or more, and evaluation of low temperature stability was A.

B: Viscosity retention was less than 80% and/or evaluation of low temperature stability was B.

The results are shown in Table 1.

TABLE 1

| Ingredients | Example No. 1 | 2 | 3 | 4 | Comparative Example No. 1 | 2 | 3 | 4 | 5 |
|---|---|---|---|---|---|---|---|---|---|
| Polyoxyethylene (196)* polyoxypropylene glycol (67)* | 20.0 | — | — | — | — | — | — | — | — |
| Polyoxyethylene (194)* polyoxypropylene glycol (39)* | — | 20.0 | — | — | — | — | — | — | — |
| Polyoxyethylene (42)* polyoxypropylene glycol (47)* | — | — | 20.0 | — | — | — | — | — | — |
| Polyoxyethylene (124)* polyoxypropylene glycol (39)* | — | — | — | 20.0 | — | — | — | — | — |
| Polyoxyethylene hydrogenated castor oil (60 E.O.) | — | — | — | — | 20.0 | — | — | — | — |
| Polyoxyethylene sorbitan monolaurate (20 E.O.) | — | — | — | — | — | 20.0 | — | — | — |
| Polyoxyethylene nonyl phenyl ether (10 E.O.) | — | — | — | — | — | — | 20.0 | — | — |
| Sucrose fatty acid ester | — | — | — | — | — | — | — | 20.0 | — |
| Diethanol amide laurate | — | — | — | — | — | — | — | — | 20.0 |
| Cetylpyridinium chloride | 0.2 | 0.2 | 0.2 | 0.2 | 0.2 | 0.2 | 0.2 | 0.2 | 0.2 |
| Polyethylene glycol #6000 (average molecular weight: 8500) | 1.0 | 1.0 | 1.0 | 1.0 | 1.0 | 1.0 | 1.0 | 1.0 | 1.0 |
| Dibasic calcium phosphate | 20.0 | 20.0 | 20.0 | 20.0 | 20.0 | 20.0 | 20.0 | 20.0 | 20.0 |
| Glycerin | 10.0 | 10.0 | 10.0 | 10.0 | 10.0 | 10.0 | 10.0 | 10.0 | 10.0 |
| Saccharin Na | 0.2 | 0.2 | 0.2 | 0.2 | 0.2 | 0.2 | 0.2 | 0.2 | 0.2 |
| Flavor | 1.0 | 1.0 | 1.0 | 1.0 | 1.0 | 1.0 | 1.0 | 1.0 | 1.0 |
| Distilled water | (up to 100%) | | | | | | | | |
| Bactericidal activity | A | A | A | A | B | B | B | B | B |
| Viscosity | 98 | 95 | 90 | 98 | 20 | 10 | 15 | 10 | 20 |

TABLE 1-continued

|  | Example No. | | | | Comparative Example No. | | | | |
|---|---|---|---|---|---|---|---|---|---|
| Ingredients | 1 | 2 | 3 | 4 | 1 | 2 | 3 | 4 | 5 |
| retention (%) | | | | | | | | | |
| Low temperature stability | A | A | A | A | B | B | B | B | B |
| Overall evaluation of low temperature stability | A | A | A | A | B | B | B | B | B |

Note:
*The number in the parentheses means average degree of polymerization.

As shown in Table 1, the dentifrice composition of the present invention has improved stability at a low temperature without loss of bactericidal activity of cetylpyridinium chloride.

EXAMPLE 5

According to the following formulation, a toothpaste was prepared by a conventional method.

| Ingredients | % by weight |
|---|---|
| Cetylpyridinium chloride | 0.1 |
| PLURONIC F127 (degree of polymerization) ethylene oxide: 196 propylene oxide: 67 | 30.0 |
| Polyethylene glycol #6000 (average molecular weight: 8500) | 1.0 |
| Dibasic calcium phosphate | 20.0 |
| Glycerin | 20.0 |
| Saccharin Na | 0.2 |
| Flavor | 1.2 |

| Ingredients | % by weight |
|---|---|
| Distilled water | up to 100% |

The composition of Example 5 also showed good bactericidal activity and low temperature stability.

EXAMPLES 6 to 13 AND COMPARATIVE EXAMPLES 6 to 11

According to a formulation as shown in Tables 2 and 3, toothpaste were prepared. In Tables 1 to 3, all amount of ingredients formulated are % by weight.

As shown in Tables 2 and 3, by formulating polyethylene glycol having average molecular weight of 2,000 to 20,000 in an proportion of 1/200 to ¼ based on the total weight of the polyoxyethylene-polyoxypropylene block copolymer, the dentifrice composition having good shape retention at a low temperature was obtained.

TABLE 2

|  | Example No. | | | | | Comparative Example No. | | | |
|---|---|---|---|---|---|---|---|---|---|
| Ingredients | 6 | 7 | 8 | 9 | 10 | 6 | 7 | 8 | 9 |
| Polyethylene glycol #20000 (average molecular weight: 20000) | 1.0 | — | — | — | — | — | — | — | — |
| Polyethylene glycol #11000 (average molecular weight: 10500) | — | 1.0 | — | — | — | — | — | — | — |
| Polyethylene glycol #6000 (average molecular weight: 8500) | — | — | 1.0 | — | — | — | — | — | — |
| Polyethylene glycol #4000 (average molecular weight: 3000) | — | — | — | 1.0 | — | — | — | — | — |
| Polyethylene glycol #2000 (average molecular weight: 2000) | — | — | — | — | 1.0 | — | — | — | — |
| Polyethylene glycol #1540 (average molecular weight: 1450) | — | — | — | — | — | 1.0 | — | — | — |
| Polyethylene glycol #1000 (average molecular weight: 1000) | — | — | — | — | — | — | 1.0 | — | — |
| Polyethylene glycol #400 (average molecular weight: 400) | — | — | — | — | — | — | — | 1.0 | — |
| Polyoxyethylene (196)* polyoxypropylene glycol (67)* | 30.0 | 30.0 | 30.0 | 30.0 | 30.0 | 30.0 | 30.0 | 30.0 | 30.0 |
| Cetylpyridinium chloride | 0.2 | 0.2 | 0.2 | 0.2 | 0.2 | 0.2 | 0.2 | 0.2 | 0.2 |
| Dibasic calcium phosphate | 20.0 | 20.0 | 20.0 | 20.0 | 20.0 | 20.0 | 20.0 | 20.0 | 20.0 |
| Glycerin | 20.0 | 20.0 | 20.0 | 20.0 | 20.0 | 20.0 | 20.0 | 20.0 | 20.0 |
| Saccharin Na | 0.1 | 0.1 | 0.1 | 0.1 | 0.1 | 0.1 | 0.1 | 0.1 | 0.1 |
| Flavor | 1.0 | 1.0 | 1.0 | 1.0 | 1.0 | 1.0 | 1.0 | 1.0 | 1.0 |
| Distilled water | | | | (up to 100%) | | | | | |
| Bactericidal activity | A | A | A | A | A | A | A | A | A |
| Viscosity retention (%) | 120.0 | 110.0 | 100.0 | 95.0 | 90.0 | 85.0 | 60.0 | 50.0 | 50.0 |
| Low temperature stability | A | A | A | A | A | B | B | B | B |
| General evaluation of low temperature stability | A | A | A | A | A | B | B | B | B |

Note:
*The number in the parentheses means average degree of polymerization.

TABLE 3

|  | Example No. | | | Comp. Example No. | |
|---|---|---|---|---|---|
| Ingredients | 11 | 12 | 13 | 10 | 11 |
| Polyethylene glycol #6000 (average molecular weight 8500) | 0.15 [1:200]** | 3.0 [1:10]** | 7.5 [1:4]** | 0.075 [1:400]** | 10.0 [1:3]** |
| Polyoxyethylene (196)* polyoxy- | 30.0 | 30.0 | 30.0 | 30.0 | 30.0 |

TABLE 3-continued

| Ingredients | Example No. 11 | Example No. 12 | Example No. 13 | Comp. Example No. 10 | Comp. Example No. 11 |
|---|---|---|---|---|---|
| propylene glycol (67)* | | | | | |
| Cetylpyridinium chloride | 0.2 | 0.2 | 0.2 | 0.2 | 0.2 |
| Dibasic calcium phosphate | 20.0 | 20.0 | 20.0 | 20.0 | 20.0 |
| Glycerin | 20.0 | 20.0 | 20.0 | 20.0 | 20.0 |
| Saccharin Na | 0.1 | 0.1 | 0.1 | 0.1 | 0.1 |
| Flavor | 1.0 | 1.0 | 1.0 | 1.0 | 1.0 |
| Distilled water | | | (up to 100%) | | |
| Bactericidal activity | A | A | A | A | A |
| Low temperature viscosity retention (%) | 90.0 | 100.0 | 90.0 | 70.0 | 100.0 |
| Low temperature stability | A | A | A | B | B |
| General evaluation of low temperature stability | A | A | A | B | B |

Note:
*The number in the parentheses means average degree of polymerization.
**Weight ratio of polyethylene glycol to polyoxyethylene-polyoxypropylene glycol

What is claimed is:

1. A dentifrice composition in the form of an aqueous gel comprising 15 to 80% by weight of a polyoxyethylene-polyoxypropylene block copolymer surfactant based on the total weight of the composition, 0.001 to 5% by weight of cetylpyridinium chloride based on the total weight of the composition, and polyethylene glycol having an average molecular weight of 2,000 to 20,000 in a proportion of 1/200 to ¼ based on the weight of the polyoxyethylene-polyoxypropylene block copolymer.

2. A dentifrice according to claim 1, wherein the block copolymer surfactant is contained in an amount of 20 to 50% by weight based on the total weight of the composition.

3. A dentifrice according to claim 1, wherein the cetylpyridinium chloride is contained in an amount of 0.01 to 0.5% by weight based on the total weight of the composition.

4. A dentifrice according to claim 1, wherein the block copolymer surfactant contains a polyoxypropylene hydrophobic group having a molecular weight of 1,400 to 4,000 and 30 to 80% by weight of a polyoxyethylene hydrophilic group based on the total weigh of the surfactant.

* * * * *